(12) United States Patent
Thomas

(10) Patent No.: US 12,109,292 B2
(45) Date of Patent: Oct. 8, 2024

(54) BIOFLAVONOID COMPOSITIONS AND THEIR USE

(71) Applicants: Oraldent Limited, Cambridgeshire (GB); Richard Thomas, Kimbolton (GB)

(72) Inventor: Howard Thomas, Cambridgeshire (GB)

(73) Assignee: ORALDENT LIMITED, Cambridgeshire (GB)

(*) Notice: Subject to any disclaimer, the term of this patent is extended or adjusted under 35 U.S.C. 154(b) by 342 days.

(21) Appl. No.: 17/286,191

(22) PCT Filed: Oct. 18, 2019

(86) PCT No.: PCT/GB2019/052982
§ 371 (c)(1),
(2) Date: Apr. 16, 2021

(87) PCT Pub. No.: WO2020/079450
PCT Pub. Date: Apr. 23, 2020

(65) Prior Publication Data
US 2023/0043687 A1 Feb. 9, 2023

(30) Foreign Application Priority Data
Oct. 18, 2018 (GB) .................................... 1817005

(51) Int. Cl.
*A61K 8/49* (2006.01)
*A61K 8/04* (2006.01)
*A61K 8/27* (2006.01)
*A61K 8/36* (2006.01)
*A61Q 11/02* (2006.01)

(52) U.S. Cl.
CPC ............. *A61K 8/498* (2013.01); *A61K 8/042* (2013.01); *A61K 8/27* (2013.01); *A61K 8/361* (2013.01); *A61Q 11/02* (2013.01)

(58) Field of Classification Search
CPC . A61K 8/60; A61K 8/73; A61K 8/602; A61K 8/27; A61P 1/02; A61Q 11/00
USPC .......................................... 424/49, 401, 641
IPC ...................................................... A61Q 11/00
See application file for complete search history.

(56) References Cited

U.S. PATENT DOCUMENTS

| | | | | |
|---|---|---|---|---|
| 5,035,882 A | * | 7/1991 | Hussein | ................ A61K 36/81 426/651 |
| 2010/0317734 A1 | | 12/2010 | Folan | |
| 2013/0085137 A1 | | 4/2013 | Grigorian | |
| 2018/0085292 A1 | * | 3/2018 | Pierce | ...................... A61J 3/07 |
| 2018/0110712 A1 | | 4/2018 | Ong | |
| 2018/0228167 A1 | | 8/2018 | King | |

FOREIGN PATENT DOCUMENTS

| | | | |
|---|---|---|---|
| CN | 101882736 A | 11/2010 | |
| CN | 102218021 B | 1/2013 | |
| CN | 106261893 | 1/2017 | |
| CN | 106360239 A | 2/2017 | |
| CN | 106619193 | * 10/2017 | ............... A61K 8/64 |
| CN | 107468584 | 12/2017 | |
| EP | 2198862 | 6/2010 | |
| GB | 2505248 | 2/2014 | |
| GB | 2507108 | 4/2014 | |
| JP | 05310544 | 11/1993 | |
| JP | 2004107309 A | 4/2004 | |
| JP | 2005152784 | 6/2005 | |
| KR | 20050063182 | 6/2005 | |
| KR | 20160007839 | 1/2016 | |
| KR | 20190011844 | 2/2019 | |
| WO | 2000011956 | 3/2000 | |
| WO | 2001015536 | 3/2001 | |
| WO | 2006117029 A1 | 11/2006 | |
| WO | 2008009956 A1 | 1/2008 | |
| WO | 2008009958 A1 | 1/2008 | |
| WO | 2010089600 A1 | 8/2010 | |
| WO | 2011067721 | 6/2011 | |
| WO | 2012017186 A1 | 2/2012 | |
| WO | 2014122446 A1 | 8/2014 | |
| WO | 2016102931 A1 | 6/2016 | |
| WO | 2020079450 A1 | 4/2020 | |

OTHER PUBLICATIONS

Najjar et al., "Natural Antimicrobials e-Poly-L-lisine and Nisin A for Control of Oral Microflora." Probiotics & Antimicrobial Proteins (2009) 1:143-147. (Year: 2009).*

Newseed Chemical Co., Limited, "EpsilonPoly L Lysine: What is polylysine, e." https://www.foodsweeteners.com>epsilon-poly-l-lysine. Published online Feb. 21, 2018 (Year: 2018).*

Ammar, et al., "Flavonoids as a possible preventive of dental plaque", Archives of Pharmacal Research, vol. 13, No. 2, 1990, pp. 211-213.

Putnik, et al., "Innovative "green" and novel strategies for the extraction of bioactive added value compounds form citrus wastes—A review", Molecules, vol. 22, No. 680,2017, pp. 1-24.

Tsui, et al., "The inhibitory effects of naringin on the growth of periodontal pathogens in vitro", Phytotherapy Research, vol. 22, 2008, pp. 401-406.

(Continued)

*Primary Examiner* — Walter E Webb

(74) *Attorney, Agent, or Firm* — FisherBroyles, LLP; Adam K. Whiting; Adelaide K. Leitzel

(57) ABSTRACT

The present invention relates to pharmaceutical compositions and their use in oral hygiene. More particularly, the compositions comprise one or more flavonoids, such as naringin and neohesperidine and polylysine and/or caprylic acid and/or a zinc salt. Such compositions may be in the form of, for example, a solution, gel, spray, chewing gum or paste suitable for use in the oral cavity. The composition may be used in reducing bacterial numbers on teeth, gums or other surfaces in the oral cavity.

10 Claims, 2 Drawing Sheets

(56) References Cited

OTHER PUBLICATIONS

Yu, et al., "Supercritical fluid extraction of liminoids and naringin from grapefruit (*Citrus paradisi* Macf.) seeds", Food Chemistry, vol. 105, 2007, pp. 1026-1103.

Yue, et al., "Influence of naringenin on the biofilm formation of Streptococcus mutans", Journal of Dentistry, vol. 76,2018, pp. 24-31.

Desbois, et al., "Antibacterial free fatty acids: Activities, mechanisms of action and biotechnological potential", Appl. Microbial. Biotechnol, vol. 85, No. 6, Dec. 3, 2009, p. 1629-1642.

Hyldgaard, et al., The antimicrobial mechanism of action of e-poly-L-lysine, Appl. Environ. Microbial., vol. 80, No. 24, Oct. 10, 2014.

JP2005-152784 translation, "Kato". (Year: 2005).

Ch Stratakos, Alexandros, et al. "The in vitro and ex vivo effect of Auranta 3001 in preventing Cryptosporidium hominis and Cryptosporidium parvum infection." Gut Pathogens 9 (2017): 1-10.

\* cited by examiner

BIOFLAVONOID COMPOSITIONS AND THEIR USE

The present invention provides compositions suitable for use in oral hygiene. More aptly, the present invention relates to compositions which contain bioflavonoids and polylysine and/or caprylic acid and/or a zinc salt suitable for improving oral health. Favoured compositions comprise naringin, neohesperidin and polylysine.

CROSS REFERENCE TO RELATED APPLICATIONS

This application is a 371 National Stage filing and claims the benefit under 35 U.S.C. § 120 to International Application No. PCT/GB2019/052982, filed 18 Oct. 2019, which claims priority to Great Britain Application No. 1817005.0, filed 18 Oct. 2018, each of which is incorporated herein by reference in its entirety.

BACKGROUND OF THE INVENTION

Various flavonoids have been suggested to possess antibacterial properties. PCT/GB2007/002756 and PCT/GB2007/002758 describe particularly effective compositions containing flavonoids.

One family of commercial products is available under the trade mark Citrox which have proved particularly advantageous in respect of antibacterial properties in the oral cavity.

Nevertheless, known bioflavonoid anti-infective agents are not always as effective as could be wished when treating certain organisms present in the oral cavity. Thus, for example an enhancement in effectiveness is often desirable in the case of particularly difficult problems such as those resulting from certain biofilm forming bacteria.

The present invention addresses such problems by providing compositions suitable for use in the mouth which comprise a bioflavonoid component and polylysine and/or caprylic acid and/or a zinc salt component.

DESCRIPTION

The present invention provides a composition which comprises polylysine and/or caprylic acid, and/or a zinc salt, and one or more flavonoids of Formula (I)

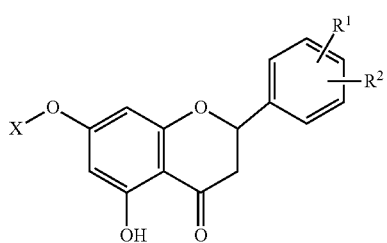

(I)

wherein $R^1$ is hydroxyl or methoxyl and $R^2$ is hydrogen, hydroxyl or methoxyl and X is hydrogen or a saccharide.

Aptly in the first component $R^2$ is hydrogen and $R^1$ is in the 3- or 4-position. Alternatively, aptly in the first component $R^2$ is 3-hydroxy and $R^1$ is 4-methoxyl.

Suitably X in a compound of the Formula (I) is H.
Suitably X in a compound of the Formula (I) is a saccharide.
Favourably X is a disaccharide.

Suitable disaccharides include combinations of two monosaccharide, suitably pyranoses, linked by a glycosidic bond, for example rhamnose and glucose, for example L-rhamnose and D-glucose.

Suitable disaccharides can have the structure:

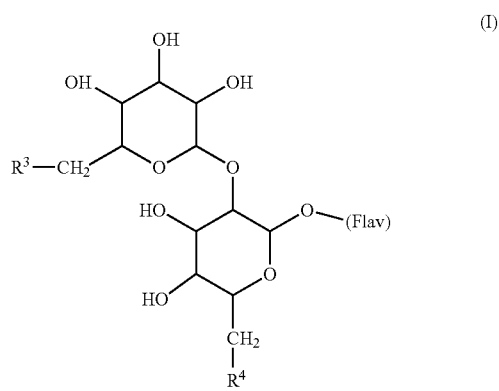

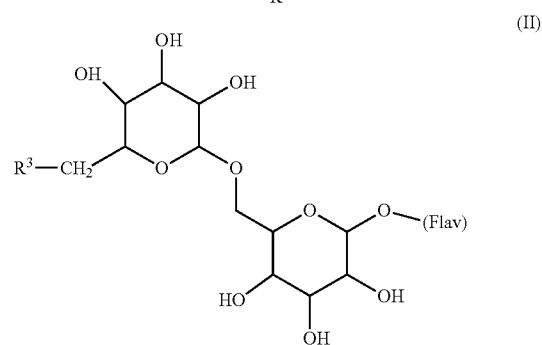

wherein one of $R^3$ and $R^4$ is H and the other OH or both are H or both are OH. Aptly $R^3$ is H and $R^4$ is OH so that the disaccharide is rutinose.

Favoured glycosyl groups of flavonoids for use in this invention are the disaccharides 6-O-(alpha-L-rhamnopyra-nosyl)-beta-D-glucopyranose, also known as rutinose, and 2-O-(alpha-L-rhamnopyra-nosyl)-beta-D-glucopyranose.

It is presently believed that the flavonoid of Formula I very suitably comprises naringin or neohesperidin or mixtures thereof. Mixtures of one or both of naringin and neohesperidin with for example, one, two or three other flavonoids of the Formula I are presently believed particularly favoured for use in this invention. Such mixtures can be obtained from extraction from bitter oranges.

Suitable compounds of Formula (I) include Neoeriocitrin, Isonaringin, Naringin, Hesperidin, Neohesperidin, Neodiosmin, Naringenin, Poncirin and Rhiofolin.

Favoured compositions for use include those which comprise either of naringin and neohespiridin or preferably both.

Particularly aptly the invention will contain naringin and neohesperidin and other flavonoids of the Formula (I).

The mixture of flavonoids may aptly contain neohesperidin and naringin, and one or more of isocriocrin, isonaringin, naringin, hesperidine, neohesperidin, neocliomin, naringenin, poncrin and rhiofolin. Such a mixture of flavonoids can be obtained from bitter oranges. Suitable mixtures can include 2, 3, 4, 5, 6, 7, 8, 9 or more compounds of Formula (I). Thus, a mixture comprising 2, 3, 5, 6, 7, 8 or 9 of the above named flavonoids is aptly, for example containing 3, or containing 4, or containing 5, or containing 6, or containing 7, or containing 8 or containing 9 of said flavonoids.

It is presently believed that mixtures of such flavonoids have advantages over the use of a single flavonoid. It is particularly advantageous that extract of bitter oranges may be employed without the need for isolating individual flavonoids if desired. The use of the composition generally comprising biomass that enhances solubility of the flavonoids. Generally, the flavonoids are present in mixtures with biomass by about 10% to 75%, more aptly 30% to 60%, for example 40% to 50%, preferably about 45%. The biomass comprises pectins and other sugar derived materials. Typically, about 40% of low molecular weight pectins are present in such biomass.

If it is desired to avoid biomass, other solubilising agents such as dextrins, for example cyclodextrin, may be employed if desired, but this is not presently envisaged as generally advantageous.

Aptly the mixture of flavonoids will comprise at least 25%, more suitably at least 40% and preferably at least 50% of naringin. More aptly the mixture will contain from 40% to 65% of naringin (wt/wt of flavonoids present).

Aptly the mixture of flavonoids will comprise at least 15%, more suitably at least 20% and preferably at least 25% of neohesperidin. More aptly the mixture will contain 20% to 35% of neohesperidin (wt/wt of flavonoid present).

In a favoured form the mixture of flavonoids will contain at least 75% of neohesperidin and naringin (wt/wt).

The composition will also comprise polylysine and/or caprylic acid, and/or a zinc salt.

Favourably, the amino acids in polylysine should be capable of forming charged polymers, for instance ε-polylysine is preferred to α-polylysine because the free amino acid groups may have a positive charge in non-basic media. Polylysine consists of 20-50, favourably 25-40 L-lysine residues with a molecular weight of 2400-6000 Da, favourably 3000 Da-5000 Da.

The concentration range of polylysine, particularly ε-polylysine employed is aptly 0.05 to 1.00 wt-%, for example 0.1 to 0.75 wt-%, such as 0.25 to 0.50 wt-%.

The concentration range of the bioflavonoids employed is aptly 0.05 to 6 wt-%, for example 0.1 to 4 wt-% such as 0.2 to 3 wt-%.

A particular advantage of many compositions of the invention is that they may employ compounds of natural origin. Thus, for example, it is preferred to employ bioflavonoids obtained from bitter oranges. However, synthetically or semi-synthetically obtained compounds may be employed if desired instead of the ones directly extracted from natural sources although this tends to be less favourable in view of cost and less acceptable to those who prefer agents which are naturally derived from renewable resources.

The compositions of this invention show synergistic antimicrobial effectiveness between the bioflavonoids and the polylysine and/or caprylic acid.

It is presently believed that the preferred range is between 30 mg/L and 240 mg/L of polylysine and 0.06% to 4% bioflavonoids as best synergy is believed to then occur.

Aptly the composition comprises flavonoids of Formula I and polylysine.

Aptly the composition comprises flavonoids of Formula I and caprylic acid.

Aptly the composition comprises flavonoids of Formula I and polylysine and caprylic acid.

Such compositions may desirably contain a mixture of for example 65% to 75% of naringin and neohesperidin together with polylysine and/or caprylic acid, and/or a zinc salt (wt/wt).

The compositions for oral use may include the polylysine, optionally together with caprylic acid and/or a zinc salt. The compositions for oral use may include caprylic acid, optionally together with polylysine and/or a zinc salt. The compositions for oral use may include a zinc salt, optionally together with polylysine and/or caprylic acid.

The caprylic acid may be employed in preparing the composition as the parent acid or a salt such as the sodium, potassium, calcium, magnesium or an amine salt of which the sodium salt is often apt.

Suitable zinc salts include zinc oxide, zinc chloride, zinc citrate, zinc acetate, zinc sulfate, zinc lactate, zinc phosphate, zinc gluconate, or a salt with an amino acid and the like.

It has been found that compositions of this invention are particularly effective in the presence of an additional component, which is one or more organic acids.

A surprisingly effective acid for use include citric acid or salicylic or lactic acid or pharmaceutically acceptable salt thereof, optionally together with a further organic acid or pharmaceutically acceptable salt.

Favourably an organic acid may be present, such as acids of up to 8 carbon atoms which are monobasic (i.e. one $CO_2H$ group), di-basic or tri-basic acid which optionally contain 1, 2 or 3 hydroxyl groups. Such organic acid may be one or more of citric acid, malic acid, lactic acid, tartaric acid, fumaric acid and the like.

Such compositions can provide an approximately neutral or acid pH, when used, for example pH of from 3-8, more aptly 3.5-7, for example 4-5.

In compositions containing a flavonoid of Formula I, polylysine and/or caprylic acid (and optionally a further organic acid, and/or a zinc salt) the weight/weight ratio of the compound(s) of Formula (I) to polylysine and/or caprylic acid to the acid or pharmaceutically acceptable salt thereof is 1300:1 to 1:10, more aptly 100:1 to 1:5, favourably 50:1 to 1:3 and preferably is 25:1 to 3:1, for example 20:1.

Such compositions may include a solubilising agent, for example a dextrin such as cyclodextrin, although use of biomass extracted from bitter oranges can avoid the need for this if required.

The compositions of the invention show activity against a wide range of organisms including gram positive bacteria, gram negative bacteria, fungi, virus, protazoans and insect parasites. Particularly surprising the compositions may be employed against difficult bacteria such as methicillin resistant *Staphylococcus aureus* (MRSA), *Clostridium difficile* (C.diff) *Helicobacter pylori* (H.py), and vancomycin resistant enterobacteria. The compositions of this invention may also be used against norovirus and other pathogens whereby transmission is by contact or air.

It is a particular advantage that the compositions are effective against film forming bacteria.

Chlorhexidine has been the biocide of choice for oral care infections, but it has a limitation in that it is not very effective against gram negative organisms such as *Streptococcus sanguis, Porphyromonas gingivalis, Tannerella forsythia, Treponema denticola, Prevotella intermedia* and *Aggregatibacter actinomycetemcomitans*, which are the main causes of gum tissue destruction, or *Helicobacter pylori*, which can lead to ulceration of the gastric tract. The bioflavonoid and polylysine compositions are broad spectrum and equally effective against gram negative and gram positive bacteria. The combination has particular use therefore in compositions for use in the oral cavity, for example to reduce the growth of the preceding bacteria.

Particularly suitably such compositions are suitable for use to treat humans, especially by oral administration, for example as a toothpaste or mouthwash.

Suitable oral compositions include those analogous to those described in PCT/GB2007/002756 and PCT/GB2007/002758.

These compositions may be in the form of solutions, gels, pastes, a spray, chewing gum, mouthwash and the like.

Such compositions may be used to reduce the bacterial count on surfaces within the oral cavity, especially where it is desirable to reduce the presence of bacteria such as *Clostridium difficile* or film forming bacteria.

The compositions may be in the form of a toothpaste, mouthwash, gel, spray or a chewing gum. These may be used in the treatment of gum disease or to reduce plaque formation. Hence their use can also aid in reducing both staining or improving the cosmetic appearance of teeth.

Thus, toothpaste and the like may aptly contain surfactants. Many conventional surfactants may be employed but it appears certain effective formulations will employ non-ionic surfactants. Particularly effective non-ionic surfactants include alkyl polycyclosides and/or alkenyl polyglycosides (APGs) such as those containing up to 10 sugar residues coupled to a hydrocarbon chain. Oligomerisation of up to about 4 sugar residues can be desirable. Such surfactants are available under the trade name "Plantacare" for example from Henkel as "Plantacare 2000".

In some compositions minor amounts of typical anionic surfactants may be employed together with the non-ionic surfactant. Amphoteric surfactants may also be present, for example and preferably, with the non-ionic surfactants, for example those having secondary or tertiary amino and water solubilising anionic groups, such as sulphate, phosphate, phosphonate or carbon/late groups. Such amphoteric surfactants include those available under trade names such as Miranol (of Rhone-Poulenc) and Betaine, such as Dehyton from Henkel.

The compositions of the invention may optionally comprise thickening agents. Suitable thickening agents include polysaccharide thickeners such as xanthan gums, gellan gums, pectins, carageenans and the like. An apt thickening agent is xanthan gum such as Keltrol CG which is a high molecular weight polysaccharide produced by microbial fermentation. Viscosity may also be selected by use of an amphoteric surfactant such as a cocamido-propyl betaine or Tego Betaine F50 as a thickening as well as surfactant agent.

EXAMPLES

Example 1

Gel

Water (481.5 g; 96.3%) was added to a beaker and stirring commenced. Keltrol CG-SFT (9.0 g; 1.8%) was added and stirring continued until dissolved. Citrox powder (2.5 g; 0.5%) was added and stirring continued until dissolved. White willow bark extract (2.0 g; 0.4%) was added and stirring continued until dissolved. Glycerol (5.0 g; 1.0%) was added and stirring continued until dissolved.

The resulting viscous gel was de-aerated. The pH was 4-5. The viscosity 7000-10000 cp at 20° C. (spindle 4/0 rpm). The pH may be adjusted with citric acid if required to bring it within the stated range.

The Willow Bark extract contains 90% of salicylic acid.

The Citrox powder (Citrox Biosciences), hereinafter Citrox, comprises 7.5% of residues of extraction from bitter oranges together with the following mixture of bioflavonoids:

| Bioflavonoid mixture | % bioflavonoid (component in biomass) |
|---|---|
| Neoeriocitrin | 1.1 |
| Isonaringin | 1.2 |
| Naringin | 23.4 |
| Hesperidin | 1.4 |
| Neohesperidin | 12.5 |
| Neodiosmin | 1.4 |
| Naringenin | 1.5 |
| Poncirin | 2.0 |
| Other (Rhiofolin) | 0.5 |
| Total | 45% |

Example 1 is repeated in the presence of zinc gluconate (0.85 wt-%).

Example 2

Foam Composition

This can be prepared by mixing ingredients as described in Example 1.

| Salicylic acid | 0.25% |
|---|---|
| Citric acid | 0.15% |
| Bioflavonoid mixture (Example 1) | 0.0375% |
| ε-Polylysine or caprylic acid | 0.015% |
| Betaine BP20 | 1.0% |
| Glycerine | 0.5% |
| Dermosoft GMCY | 1.0% |
| Water | 97.0% |

ε-Polylysine is from Everguard PL, Impag AG.

When tested against spores of *Clostridium difficile* (NCTC 11209) according to BS EN 13704, satisfactory sporicidal activity was found with a 15 minutes contact time at 20° C.

Example 3

Sanitizing Gel

This can be prepared by mixing as described in Example 1.

| Keltrol CG-SFT | 1.7% |
|---|---|
| Bioflavonoid mixture (Example 1) | 0.0375% |
| ε-Polylysine or caprylic acid | 0.015% |
| Citric acid | 0.15% |
| Salicylic acid | 0.25% |
| Dermosoft GMCY | 1.0% |

| | |
|---|---|
| Glycerine | 1.0% |
| Water | 95.8% |

Such a gel provides satisfactory sporicidal activity against the spores of *C. difficile*.

Example 4

Toothpaste Formulation

| Raw Material | wt-% |
|---|---|
| Water | 29.499 |
| K2 HPO4 | 0.290 |
| KH2PO4 | 0.580 |
| Veegum D | 2.000 |
| Stevia | 0.080 |
| Sodium Fluoride 950 ppm | 0.229 |
| Citric acid | 0.200 |
| Sodium benzoate | 0.150 |
| Disodiummonohydrogenphosphate | 0.500 |
| Sodium chloride | 0.330 |
| Hombitan AFDC 170 nm | 1.000 |
| Sorbitol 70% solution | 26.700 |
| Genuvisco TPC1 | 0.500 |
| Glycerine | 12.650 |
| Mulsifan csa20 | 4.000 |
| Sident 8 | 12.000 |
| Sident 22 5 | 8.077 |
| Aroma | 0.700 |
| Citrox | 0.500 |
| ε-Polylysine | 0.015 |

Example 4 is repeated in the presence of zinc gluconate (0.85 wt-%).

Example 5

Figure 1:
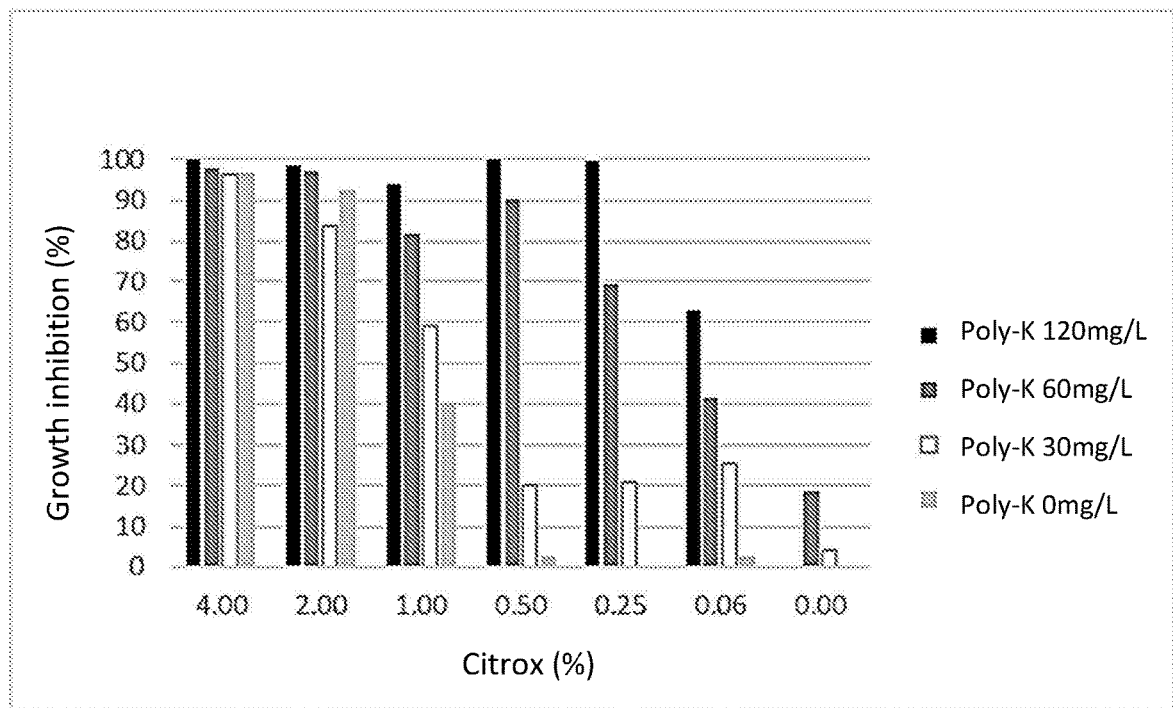
FIG. 1 shows the inhibitory effect on *Escherichia coli* growth of pretreatment at different concentrations of Citrox and/or ε-polylysine in a high binding microtiter plate.

Immobilisation and Release of Antibacterial Activity of Citrox in Presence of ε-Polylysine High Binding plates were pre-treated with 0.1 mL of pure Citrox/ε-Polylysine solutions incubated 60' at room temperature. The concentrations of Citrox range from 0.06% to 4%. The ε-Polylysine concentrations range from 30 mg/L to 120 mg/L. The wells have been emptied and rinsed with 0.2 mL bi-distilled water. 0.2 mL of a diluted *Escherichia coli* culture (turbidity: 5 m OD at 600 nm) were given to the pre-treated wells and incubated for 3 hours at 37° C. Turbidity were measured at 600 nm and percentage of growth inhibition in comparison to untreated well calculated (FIG. 1).

Example 6

Antibacterial Activity of Citrox and ε-Polylysine Against *Escherichia coli*

The antibacterial activity of Citrox and ε-Polylysine has been tested by incubating 0.2 mL mini cultures of *Escherichia coli* (0.1 OD$_{600nm}$) with varying concentrations of antibacterial substances. Growth inhibition was monitored by measuring turbidity of mini cultures after 5 hours of aerobe incubation at 37° C. under agitation. Solutions were diluted to the half in cascade. The lowest concentration of the substance yielding less than 2% (6% in case of ethanol) of growth in comparison to an untreated control is considered the minimal inhibitory concentration (MIC).

Short-Term Antibacterial Activity of Citrox Toward *S. mutans* (Bactericidal Effect)

TABLE 1

Figure 2:
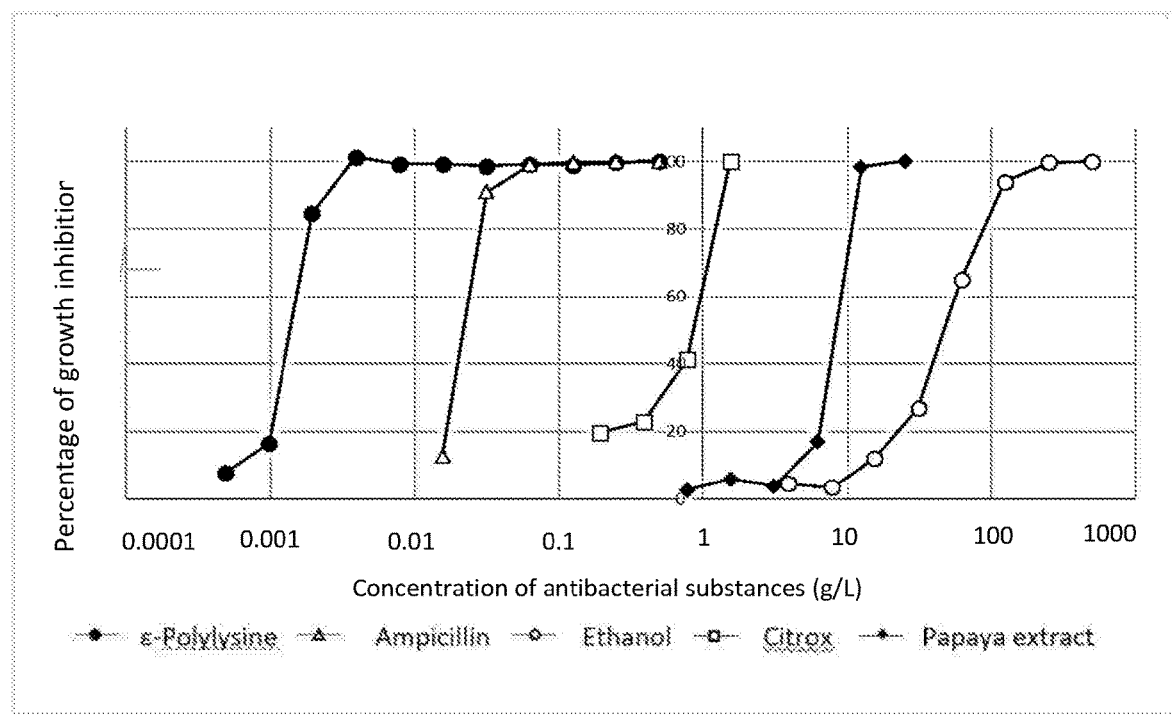
FIG. 2 shows the inhibitory effect on bacterial growth (*E. coli*) of direct exposure to Citrox or ε-polylysine compared to other antibacterial substances.

Summary of MIC (*E. coli*) extrapolated from FIG. 2 (1% corresponds to 10 g/L). Minimal inhibitory concentration (MIC)

| | |
|---|---|
| ε-Polylysine | 4 mg/L |
| Ampicillin | 60 mg/L |
| Ethanol | 12.5% |
| Citrox | 0.16% |
| Papaya extract | 1.25% |

The concomitant pretreatment with Citrox and ε-polylysine emphasizes the effectivity of Citrox pre-treatment. The apparent MIC of pretreating Citrox (0.25% pretreating Citrox with ε-polylysine 120 mg/L) approaches MIC of Citrox in directed exposure (0.16%).

With ε-polylysine 60 mg/L, 0.5% pretreating Citrox is required to reach inhibition, which is still significantly lower than the 2% required in absence ε-polylysine.

30 mg/L ε-polylysine corresponds to the highest concentration that does not affect significantly the antibacterial effect of Citrox pretreatment. Therefore, the preferred range of synergy is between 30 mg/L and 240 mg/L of ε-polylysine, and 0.06% to 4% of Citrox.

Example 7

Figure 3:
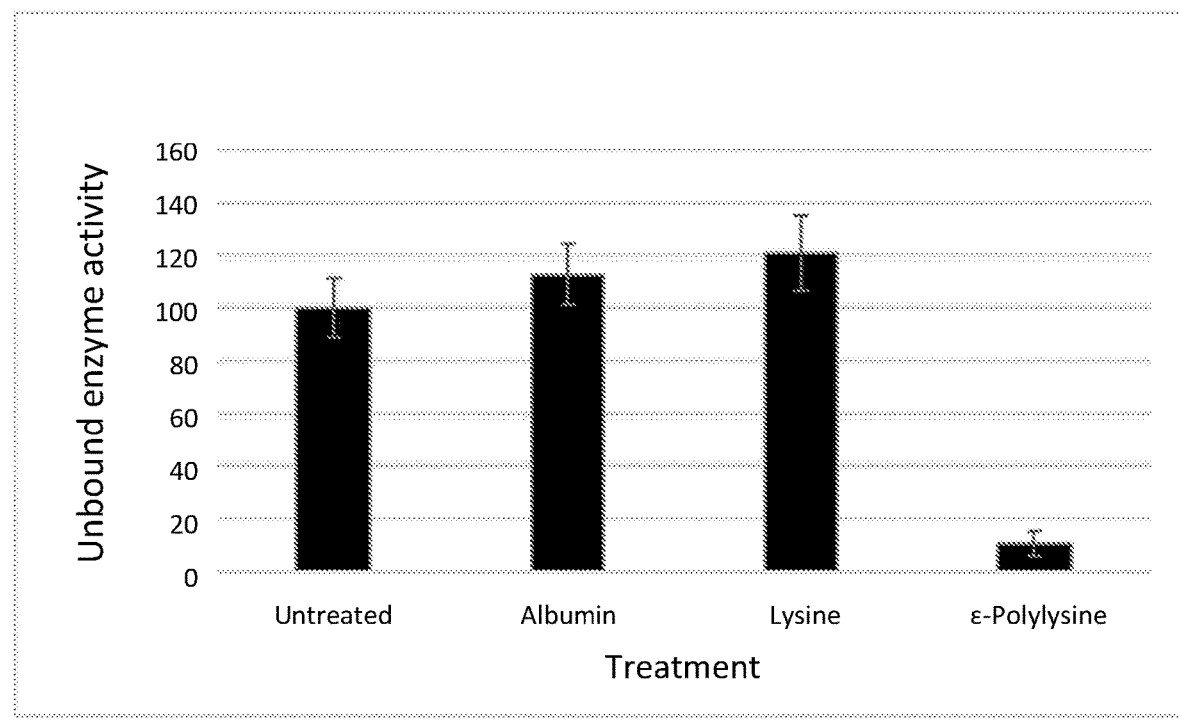
FIG. 3 shows that ε-polylysine promotes immobilization of Glucose oxidase onto silicate as assessed by measurement of residual activity in solution.

Immobilisation of Enzymatic Activity in Presence of ε-Polylysine 0.5 mg/mL glucose oxidase enzyme was incubated for 15 minutes at room temperature in an artificial saliva buffer composition including:

| | |
|---|---|
| Na$_2$HPO$_4$ | G/L 0.26 |
| NaCL | 6.70 |
| KSCN | 0.33 |
| KH2PO4 | 0.20 |
| KCL | 1.20 |
| NaHCO3 | 1.50, | with 2 mg/mL silicate and 0.25 mg/mL of an amino acid based compound, bovine serum albumin (BSA), lysine or ε-polylysine. The mixture was centrifuged in order to pellet the silicate and the supernatant tested for its glucose oxidase activity in presence of glucose, lactoperoxidase and a chromogen substrate (ABTS). The resulting activities were compared with the enzyme incubated with silicate in absence of an amino acid compound (FIG. 3).

Example 8

Antibacterial Activity of ε-Polylysine Against *S. mutans*

The antibacterial activity of ε-polylysine was semi-quantitatively assessed in a inhibition zone assay. 0.1 mL of a confluent *Streptococcus mutans* culture was spread over a Brain Heart Infusion (BHI) agar plate. Filter platelets (5 mm diameter) soaked with 0.01 mL substance were applied on plate. Plates were incubated 48 h at 37° C. under anaerobe conditions. The diameter of outer limit of the inhibition zones were measured, the diameter of the platelet deduced and the half result considered the radius of inhibition rings. Concentrations were tested in triplicate and their results averaged.

TABLE 2

Radius of inhibition rings around platelets diffusing the corresponding antibacterial substance across a *Streptococcus mutans* culture on agar plate.

| Antibacterial substance | Radius |
|---|---|
| ε-Polylysine 1000 mg/L | 6.5 mm |
| ε-Polylysine 100 mg/L | 2.5 mm |
| ε-Polylysine 10 mg/L | 0.5 mm |
| Ethanol | 5 mm |
| Water peroxide 0.1% | 1.5 mm |
| Water peroxide 1% | 5 mm |

Repetition of the preceding test with inclusion of Citrox substantially increases the radius of antibacterial inhibition.

Example 9

Short-Term Antibacterial Activity of Citrox Against *S. mutans* (Bactericidal Effect)

The short-term antibacterial activity of Citrox was semi-quantitatively assessed in a short exposure assay. A *S. mutans* culture, diluted in order to contain 5000 Colony Forming Units, was incubated for 10 minutes in presence of the antibacterial substance and extemporarily plated onto a BHI agar plate. Plates were incubated at 37° C. under anaerobe conditions and colony counted. Citrox at final concentrations of 5% resulted in complete absence of colony formation, as did water peroxide 0.05% under the same conditions. Citrox 0.5% reduced the count of CFU to the half (<3000 CFU).

Example 10

Antibacterial Effect Upon Delayed Release of Citrox is Enhanced by ε-Polylysine

The tests were performed on a plate upon which ε-polylysine strongly absorbs onto its solid surface and is not significantly released in solution. It therefore does not affect the growth of bacteria in suspension, although it prevents the surface from being colonized by bacteria.

The tests results demonstrate that the antibacterial activity of Citrox is retained by the high binding plates but also allows its release in solution, thus allowing to affect the growth of the bacteria in suspension, as well as on the solid surface. Quantitatively, pre-treating a high binding plate with Citrox 2% reaches the same inhibitory effect of a direct exposure with Citrox 0.16% (MIC Citrox).

Example 11

Tested concentrations of Citrox and ε-Polylysine employed are as follows:

| Sample No. | Citrox wt-% | Polylysine wt-% |
|---|---|---|
| 1 | 4 | 0.012 |
| 2 | 4 | 0.06 |
| 3 | 4 | 0.03 |
| 4 | 4 | 0 |
| 5 | 2 | 0.012 |
| 6 | 2 | 0.06 |
| 7 | 2 | 0.03 |
| 8 | 2 | 0 |
| 9 | 1 | 0.012 |
| 10 | 1 | 0.06 |
| 11 | 1 | 0.03 |
| 12 | 1 | 0 |
| 13 | 0.5 | 0.012 |
| 14 | 0.5 | 0.06 |
| 15 | 0.5 | 0.03 |
| 16 | 0.5 | 0 |
| 17 | 0.25 | 0.012 |
| 18 | 0.25 | 0.06 |
| 19 | 0.25 | 0.03 |
| 20 | 0.25 | 0 |
| 21 | 0.06 | 0.012 |
| 22 | 0.06 | 0.06 |
| 23 | 0.06 | 0.03 |
| 24 | 0.06 | 0 |
| 25 | 0 | 0.012 |
| 26 | 0 | 0.06 |
| 27 | 0 | 0.0 |
| 28 | 0.06 | 0 |

These demonstrated that using both agents proved antibacterially more effective than the control tests employing singular composition comprising either Citrox or ε-Polylysine (sample No 4, 8, 12, 20, 24-28).

Example 12

Sterile deionised water was inoculated with a range of different microorganisms of concern in drinking water. The inoculated water was held at 20° C. overnight to allow the cells to acclimatise. The water was then treated with different concentrations of Citrox or Citrox with caprylic acid. The concentrations used were 0.05, 0.1, 0.25, 0.5 and 1.0%. The inoculated water containing the antimicrobial was held at 20° C. for three hours. The same inoculated water, without added antimicrobial, but still held at 20° C. for three hours, was used as a control. The inoculated microorganisms were enumerated after the three-hour hold time to determine the level of inactivation. The entire experiment was repeated on two separate occasions. Further details for each type of microorganism are given below.

*Escherichia coli*

Sterile deionised water was inoculated with a 5-strain cocktail of these pathogenic strains:
  NCTC 9706
  NCTC 9707
  NCTC 11601
  NCTC 11602
  NCTC 11603

The strains were grown for 18 h at 37° C. in tryptone soya broth+0.6% yeast extract (TSBYE). Cells in stationary phase were harvested by centrifugation, washed in PBS and diluted in an appropriately sterile deionised water to give an initial inoculum level of approximately 105-106 CFU/ml. Enumeration was by spread plating on tryptone soya agar+ 0.6% yeast extract (TSAYE), with incubation at 37° C. for 24 h.

*Enterococcus faecalis*
  NCTC 8213

This strain was grown, inoculated and enumerated as described for *E. coli*.

Sulphite-Reducing *Clostridia*

Sterile deionised water was inoculated with a cocktail containing the following four species:
  *Clostridium perfringens* ATCC 13124
  *Clostridium sporogenes* NCIMB 532
  *Clostridium tyrobutyricum* DSM 663
  *Clostridium bifermentans* NCTC 506

Broth cultures were grown in cooked meat medium+1% glucose (steamed to remove oxygen and cooled before use) which was incubated anaerobically for 18 h at 37° C. Cells were harvested by centrifugation, washed in PBS and diluted appropriately in sterile deionised water to give an initial inoculum level of approximately 105-106 CFU/ml. Enumeration was by spread plating on TSAYE, incubated anaerobically at 37° C. for 24 h.

Yeasts

Sterile deionised water was inoculated with a cocktail containing the following five species:

Candida tropicalis NCYC 4
Candida solani NCYC 2570
Rhodotorula glutinis NCYC 60
Metschnikowia pulcherrima NCYC 371
Debaryomyces hansenii NCYC 9

Broth cultures were grown in malt extract broth which was incubated in an orbital incubator for 72 h at 25° C. Cells were harvested by centrifugation, washed in PBS and diluted appropriately in sterile deionised water to give an initial inoculum level of approximately 105-106 CFU/ml. Enumeration was by spread plating on malt extract agar, incubated aerobically at 25° C. for 72 h.

Vibrio parahaemolyticus

Sterile deionised water was inoculated with a cocktail containing the following four strains:

Vibrio parahaemolyticus NCTC 1165
Vibrio parahaemolyticus NCTC 1902
Vibrio parahaemolyticus AHPND A3
Vibrio parahaemolyticus AHPND D4

These strains were grown, inoculated and enumerated as described for E. coli.

Results (Reduction in Counts after 3 hr Exposure)

The Citrox reduced counts by from 3.5 log order at 0.1% to 6.5 log orders at 1%. For the formulation also comprising caprylic acid, the reductions were increased by about 1 log order.

The Citrox reduced counts of Enterococcus faecalis by 4 log orders at 0.1% to 7 log orders at 1%. For the formulation also comprising caprylic acid, the reductions were increased by about 0.7 log orders.

The Citrox reduced counts of Clostridia by 2 log orders at 0.1% and 3 log orders at 1%. For the formulation also comprising caprylic acid, the reductions were increased by about 0.5 log orders.

The Citrox reduced counts of yeast by 2 log orders at 0.1% and 6 log orders at 1%. For the composition also comprising caprylic acid, the reductions were increased by about 0.5 log orders.

The Citrox reduced counts of V. parahaemolyticus by 1.2 log order at 0.1% and 6 log orders at 1%. The composition also comprising caprylic acid increased the reductions by 0.4 log orders at 0.1% and 0.8 log orders at 2%.

Example 13

Water was sampled from three separate locations on an urban river assumed to have a relatively high microbial load. These water samples were treated with 1% w/w Citrox and 1% w/w Citrox with caprylic acid for three hours at 20° C. The following enumerations were determined in the water with and without added antimicrobials.

Total count: yeast extract agar incubated at 37° C. for 48 h

Coliforms: VRB agar with overlay incubated at 37° C. for 24 h

E. coli: TBX agar incubated at 37° C. for 24 h

Sulphite-reducing Clostridia: TSC agar with overlay incubated anaerobically at 37° C. for 24 h Enterococci: Slanetz and Bartley agar incubated at 37° C. for 4 h and then at 44° C. for 44 h Pour plating was used for all enumerations of naturally contaminated water to lower the limit of detection.

Results

Inactivation of Microorganisms in Contaminated Water

Coliforms were present at a level of 2.6 log in untreated water and were significantly reduced with Citrox and Citrox plus caprylic acid, with none detected after treatment. Results for E. coli were similar to coliforms, with initial counts of around 2 log reduced to below the limit of detection (1 CFU/ml) after treatment. Numbers of Enterococci were reduced from 1.6 log to below the limit of detection after treatment with both formulations.

The invention claimed is:

1. A composition suitable for use in the oral cavity for treating a condition selected from the group consisting of gum disease and plaque formation wherein the composition comprises ε-polylysine of molecular weight of 3000 Da to 5000 Da and caprylic acid, and a mixture of flavonoids extractable from bitter oranges comprising neoeriocitrin, isonaringin, naringin, hesperidin, neohesperidin, neodiosmin, naringenin, poncirin and rhiofolin, and wherein the ratio of flavonoids to &-polylysine and caprylic acid is 25:1 to 3:1 (wt/wt), and the concentration of flavonoids is 0.05 to 6 wt-%.

2. A composition as claimed in claim 1 which comprises a mixture of flavonoids comprising 40% to 65% of naringin (wt/wt of flavonoids) and 20% to 35% of neohesperidin (wt/wt of flavonoids present).

3. A composition as claimed in claim 1 wherein the composition comprises 0.06% to 4% of bioflavonoids and 30 mg/L to 240 mg/L of ε-polylysine.

4. A composition as claimed in claim 1 for use in reducing bacterial numbers on teeth, gums or other surfaces within the oral cavity.

5. A composition for use as claimed in claim 4 in the form of a solution, gel, spray, chewing gum or paste.

6. A composition for use as claimed in claim 4 in the form of a toothpaste or mouthwash.

7. A toothpaste or mouthwash which comprises a composition as set forth in claim 1.

8. A toothpaste or mouthwash as claimed in claim 7 for use in treating gum disease or reducing plaque formation.

9. A gel, a spray or a chewing gum which comprises a composition as set forth in claim 1.

10. A gel, a spray or a chewing gum as claimed in claim 9 for use in treating gum disease or reducing plaque formation.

* * * * *